(12) United States Patent
Mollenauer et al.

(10) Patent No.: US 6,866,672 B2
(45) Date of Patent: Mar. 15, 2005

(54) SUTURE WELDING DEVICE

(75) Inventors: Kenneth H. Mollenauer, Saratoga, CA (US); Theodore Kucklick, Saratoga, CA (US)

(73) Assignee: Starion Instruments, Corp., Saratoga, CA (US)

( * ) Notice: Subject to any disclaimer, the term of this patent is extended or adjusted under 35 U.S.C. 154(b) by 0 days.

(21) Appl. No.: 10/215,679

(22) Filed: Aug. 10, 2002

(65) Prior Publication Data

US 2002/0188304 A1 Dec. 12, 2002

Related U.S. Application Data

(60) Continuation of application No. 09/596,487, filed on Jun. 19, 2000, now Pat. No. 6,432,115, which is a division of application No. 09/286,484, filed on Apr. 5, 1999, now Pat. No. 6,077,277.

(51) Int. Cl.[7] .............................................. A61B 17/04
(52) U.S. Cl. ...................................... 606/148; 606/137
(58) Field of Search ................................ 606/139, 144, 606/145, 146, 147, 148, 113

(56) References Cited

U.S. PATENT DOCUMENTS

| | | | |
|---|---|---|---|
| 4,662,068 A | 5/1987 | Polonsky | 30/124 |
| 5,226,908 A | 7/1993 | Yoon | 606/141 |
| 5,336,221 A | 8/1994 | Anderson | 606/27 |
| 5,417,700 A | 5/1995 | Egan | 606/144 |
| 5,565,122 A | 10/1996 | Zinnbauer et al. | 219/227 |
| 5,713,908 A | 2/1998 | Jameel et al. | 606/148 |
| 5,735,875 A | 4/1998 | Bonutti et al. | 606/232 |
| 5,759,188 A | 6/1998 | Yoon | 606/147 |
| 5,814,052 A * | 9/1998 | Nakao et al. | 606/113 |
| 5,914,062 A | 6/1999 | Von Der Heyde | 219/227 |
| 6,142,957 A * | 11/2000 | Diamond et al. | 600/567 |
| 6,286,746 B1 * | 9/2001 | Egan et al. | 606/139 |
| 6,432,115 B1 * | 8/2002 | Mollenauer et al. | 606/148 |
| 2002/0035371 A1 * | 3/2002 | Westhaver et al. | 606/148 |

* cited by examiner

Primary Examiner—Julian W. Woo
Assistant Examiner—Jessica R. Baxter
(74) Attorney, Agent, or Firm—K. David Crockett, Esq.; Crockett & Crockett

(57) ABSTRACT

Devices for welding suture segments in lieu of tying knots in sutures applied during endoscopic surgery. The devices provide for snaring loose suture ends and drawing the suture ends into a space between heating surfaces, and provide for closing the heating surfaces.

13 Claims, 4 Drawing Sheets

SUTURE WELDING DEVICE

This application is a continuation of U.S. application Ser. No. 09/596,487 filed Jun. 19, 2000, now U.S. Pat. No. 6,432,115, which is a divisional of U.S. application Ser. No. 09/286,484 filed Apr. 5, 1999, now U.S. Pat. No. 6,077,277.

FIELD OF THE INVENTIONS

The devices described below relate to the field of surgical devices and methods, specifically to the field of endoscopic suturing techniques.

BACKGROUND OF THE INVENTIONS

Sutures and stitching are well known techniques for repairing body tissue after injury or surgery. Many types of surgery, such as gall bladder removal, hernia repair, and even coronary bypass surgery can now be performed through the techniques of endoscopic surgery. Endoscopic surgery, also referred to as laparoscopic surgery, minimally invasive surgery, or bloodless surgery, is performed through small incisions in the body with long slender cutting and grasping devices which can be inserted into the body through the small incisions. The devices have small working mechanisms on the distal end (the end of the instrument that is inserted into the body) and convenient handles and operating mechanisms (for controlling the working mechanisms on the proximal end). Surgeons use endoscopic scalpels and scissors for cutting tissue, endoscopic graspers and forceps for grabbing and manipulating tissue, and endoscopic suture needles for stitching tissue. Stitching a surgical or traumatic wound closed within an endoscopic work space requires quite a bit of manual dexterity and experience, and the final process of tying a knot in the stitching is very difficult.

Several devices have been suggested for assisting surgeons in securing the loose ends of a suture during open surgery. Rather than assisting the surgeon to tie a knot, the devices allow the surgeon to melt the two loose ends of the suture together or to create a melted mass on a single loose suture tip which prevents it from being withdrawn into the suture pathway. Zinnbauer, et al, Suture Cutting and Cauterizing Method Using Radiant Heat, U.S. Pat. No. 5,565,122 (Oct. 15, 1996), while not intended or adapted for endoscopic use, shows a device with jaws mounted at the distal end of a long neck, and a heating element over the jaws. When the jaws are laid against the skin, and the suture is place between the jaws, the heating element is heated to melt the suture and leave a melted mass of suture material on the suture. The melted mass prevents the suture from being pulled into and through the suture line. Polonsky, Suture Fusing and Cutting Apparatus, U.S. Pat. No. 4,662,068 (May 5, 1987) shows a pair of forceps with heat fusing surfaces on the grasping surfaces of the jaws. The forceps are used to grab and twist two loose suture ends and melt them together to secure the stitching.

SUMMARY

The devices and methods described below permit the closure of stitches during endoscopic surgery. The devices are endoscopic tools capable of insertion into an endoscopic access port, such as a cannula, and include a long slender insertion rod with a handle and operating mechanism on the proximal end and a pair of grasping jaws on the distal end of the rod. The grasping jaws are fitted with heating surfaces which can be heated to temperatures sufficient to melt suture. A snare comprised of a snare portion and a rod is housed within the insertion rod. The snare portion can be pushed out the distal end of the insertion rod and manipulated to snare a length of suture and then pulled proximally into the insertion rod. The snare may be twisted to create a length of twisted-together suture. Because the snare is drawn into the insertion rod, the entrapped suture is pulled into the space between the jaws where it can be grasped and melted by the jaws. This provides an easy way to get the suture between the jaws with limited movement of the insertion rod within the body and the endoscopic access port. The suture may be tensioned as desired by the surgeon prior to melting by closing the jaws firmly on the suture while drawing the snare proximally, then closely the jaws tightly so that the suture is held in properly tensioned position while the weld is accomplished.

In one embodiment, the jaws can be scissor-like, having opposing grasping faces which meet to clamp the suture between the grasping faces. In another embodiment, the grasping faces are mounted on co-axially disposed tubes, where the tubes rotate relative to the each other to bring the grasping faces together and close upon the suture.

A composite weldable suture is described below which is particularly useful in the creating of melted knots. The suture comprises a core, which melts at moderately high temperatures compared to a porous fiber cover, which melts at a high temperature. When two strands of suture are pressed together and exposed to heat, as in the operation of the suture welding devices, the cores melt and seep through the fiber cover and fuse together. The presence of the fiber provides structural integrity to the suture which ensures that the melted knot does not separate from the standing part of the suture.

DETAILED DESCRIPTION OF THE INVENTIONS

Figure 1:
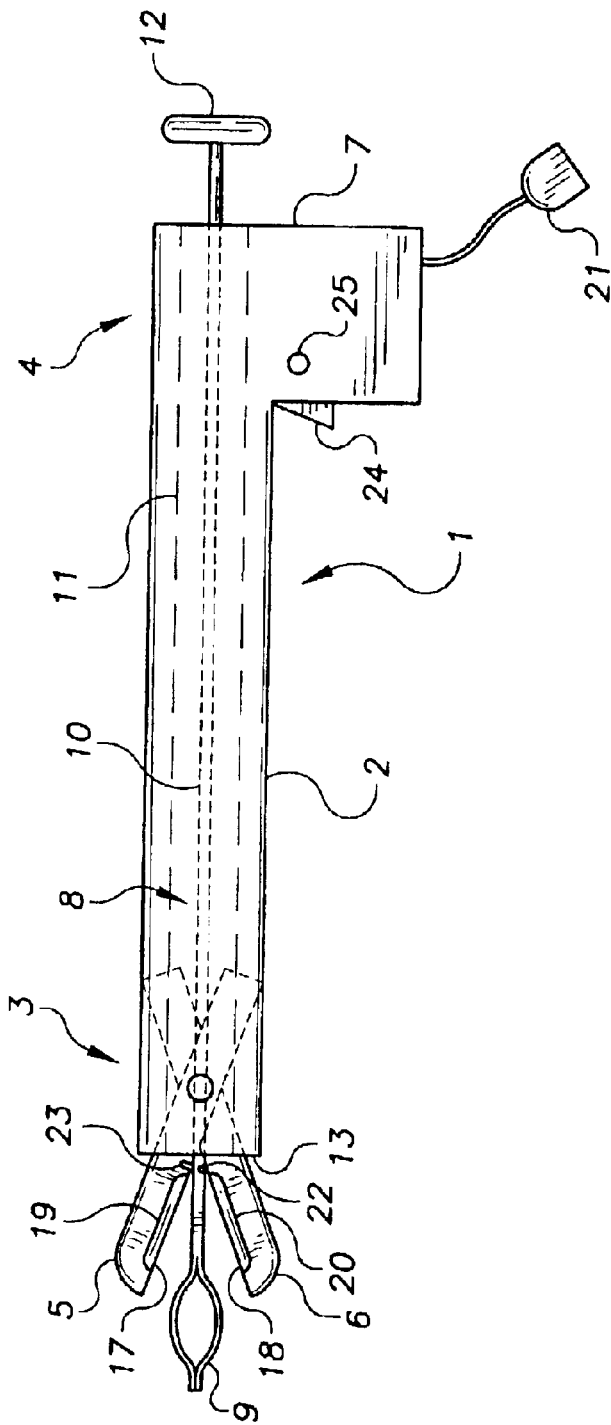
FIG. 1 illustrates a suture welding device for grabbing sutures within and endoscopic work space and fusing a knot in the suture.

FIG. 1 illustrates a suture welding device 1. The welding device is comprised of a long insertion rod 2, with a distal end 3 and a proximal end 4. The distal end carries a pair of grasping jaws 5 and 6 mounted pivotably within the distal end and protruding from the distal end of the insertion rod. The proximal end is fitted with a handle assembly 7. A snare 8 including a snaring portion 9 mounted on the distal end of a snare rod 10 15 slidably and rotatably disposed within the lumen 11 in the insertion rod 2. The snare also includes the handle 12 mounted on its proximal end. The snare exits out the distal end of the insertion rod, and as illustrated exits through a port in the distal face 13 of the insertion rod. The snare provides a means for initially grasping loose suture ends and drawing the suture ends into close proximity to the jaws. The jaws provide a second means for grasping the suture ends after they have been picked up by the snare.

The insertion rod may be any convenient length, typically 30 to 100 centimeters, and is preferably of small diameter about 2 mm to 2 cm to fit in standard endoscopic access cannulas. The lumen of the insertion rod may also be configured to exit out the side-wall of the insertion rod, thereby directing the snare rod outwardly in a direction which is divergent from the long axis of the insertion rod. The snare portion 9 is comprised of two arcuate branches of resilient metal or plastic, with each branch extending distally from the snare rod to curve first outwardly from the long axis of the snare rod and then inwardly toward the long axis of the snare rod to join together at their distal tips. The resilient branches may preferentially open upon exit from the lumen, and be compressible into a narrow configuration upon withdrawal into the lumen. The grasping jaws mounted on the distal end of the insertion rod extend distally from the insertion rod. Each jaw 5 and 6 has a grasping face 17 and 18 which opposes the grasping face on the other jaw, and the jaws may be closed to bring the grasping faces into contact or close proximity. The grasping face of each jaw includes resistive heating elements 19 and 20 which are connected to an appropriate power supply through electrical wires that run through the jaws and the insertion rod to electrical connector 21 in the handle. The lower jaw 6 holds a suture cutting blade 22 aligned with blade channel 23 on the upper jaw 5. The grasping faces may have a serrated, knurled or ridged surface to assist in holding the sutures. The handle assembly 7 may include any comfortable gripping structure such as a pistol grip or scissor handle, a trigger 24 for operating the jaws, and a switch 25 for applying electrical power to the heating elements.

Figure 2:
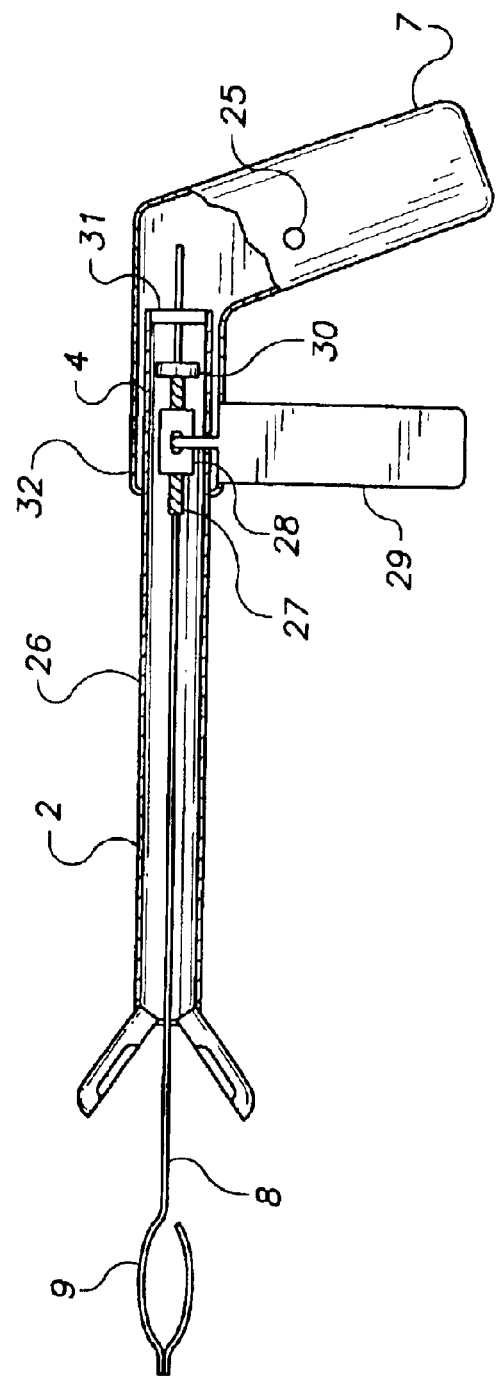
FIG. 2 illustrates a proximal handle design which permits one handed operation of the suture welding device.

FIG. 2 illustrates a proximal handle design which permits one handed operation of the suture welding device. The insertion rod 2 comprises a barrel which houses the snare 8 and the operating rod 26 for the jaws (which is pulled proximally to close the jaws). The handle assembly 7 is mounted on the proximal end 4 of the insertion rod. The snare is fixed to a screw 27, so that rotation of the screw results in rotation of the snare. The screw has high pitch threads, and slide yoke 28 engages the threads so the longitudinal movement of the slide yoke causes rotation of the screw and snare. When the trigger 29 and yoke are pulled distally, the yoke eventually meets the stop plate 30 mounted on the proximal end of the screw, and further proximal movement of the trigger results in withdrawal of the snare loop 9 into the insertion rod. At this point, the jaws of the device are open, the snare has rotated to form a twist in any suture segments ensnared in the snare loop, and the snare loop has been pulled into the insertion rod. Further proximal travel of the trigger and slide yoke will cause the yoke (and the stop plate) to engage the stop plate 31 which is fixed to the jaw operating rod 26, and force the operating rod proximally, thereby closing the jaws. The slide yoke is fixed to the trigger 24 through a slot in the handle assembly barrel 32 and the proximal end of the insertion rod. The trigger is slidably mounted in the handle assembly, and is biased to moved distally when not held or squeezed by the surgeon. The bias may be provided with spring clips or spring loaded slides, or various other arrangements. When the jaws are closed upon the sutures, the surgeon may heat the heating elements by operating a push button switch 25. While the device is illustrated with a grasper having two opposing jaws, it may be constructed with three or more grasping jaws in mutually opposing relationship. Likewise, although the snare loop is illustrated as a two-armed snare, the snare may be constructed with three or more arms which may be used to ensnare loose suture ends. Additionally, while the operation of the devices is illustrated with a typical suture structure which requires joining two standing parts of the suture structure, three or more standing parts may be joined in the melted "knot" created by the device.

Figure 3:
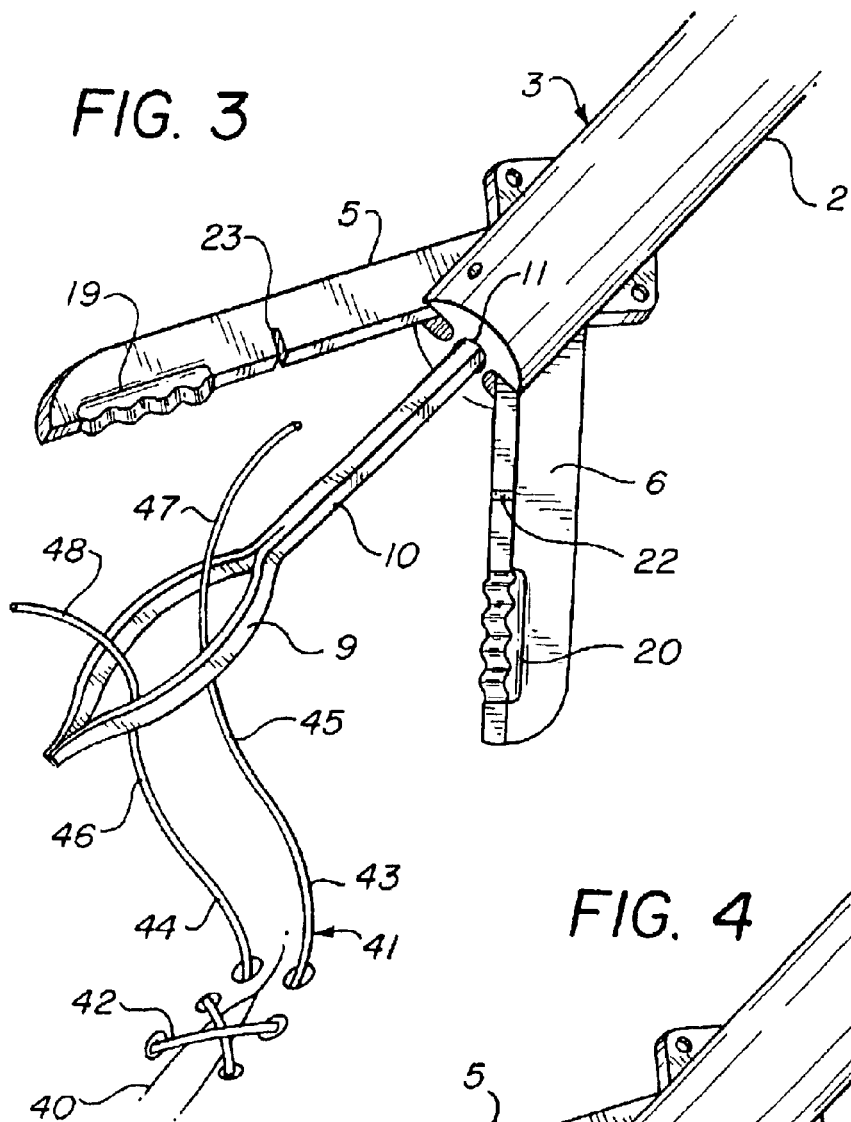
FIG. 3 illustrates a step in the operation of the suture welding device of FIG. 1.
Figure 4:
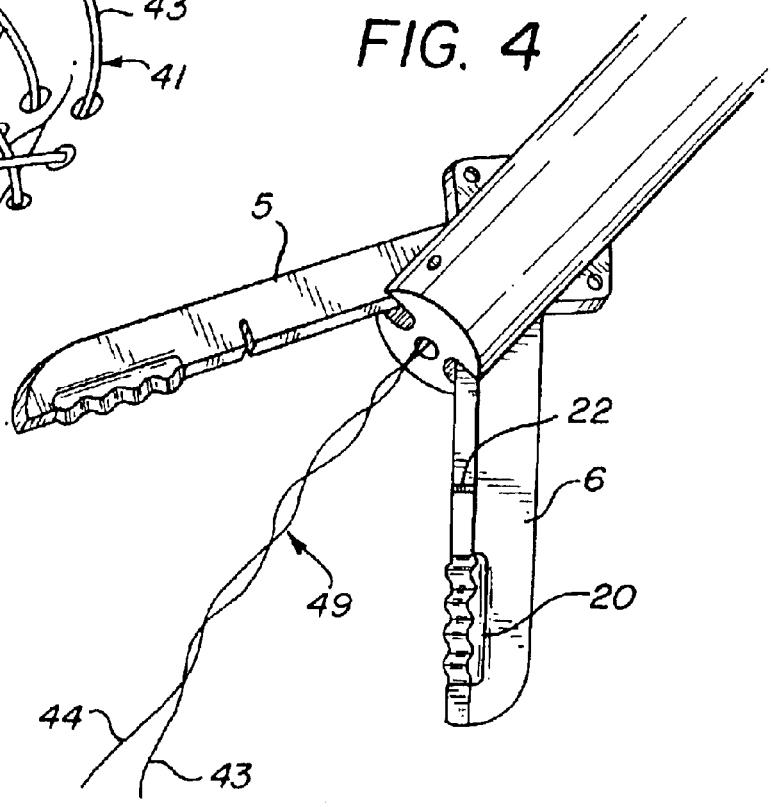
FIG. 4 illustrates a step in the operation of the suture welding device of FIG. 1.
Figure 5:
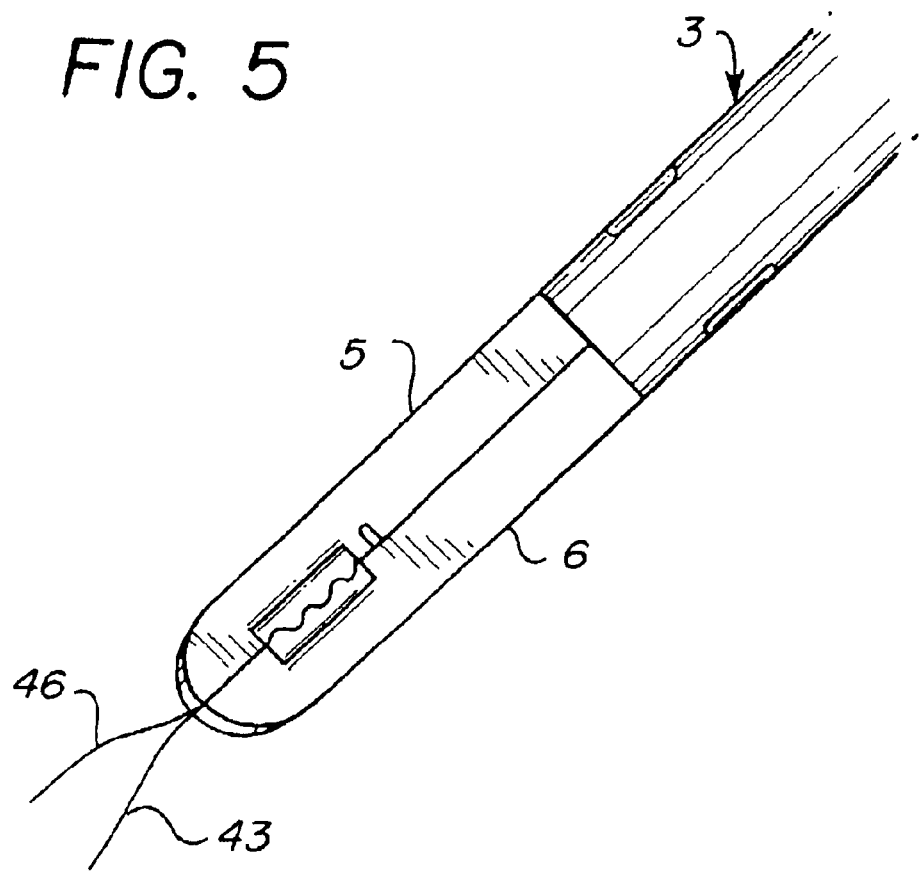
FIG. 5 illustrates a step in the operation of the suture welding device of FIG. 1.

FIGS. 3, 4 and 5 illustrate the use of the suture welding device. In FIG. 3 the distal end of the insertion rod is illustrated in proximity to a surgical incision 40 which has been stitched with suture 41. The suture 41 may be any fusible suture, including the suture described below in reference to FIG. 10. The suture segments may be referred to as the stitches 42, the standing parts 43 and 44 (which are the lengths of suture remaining after the knot is welded), the welding portions 45 and 46 and the ends 47 and 48 (the ends are removed after the knot is welded). The snare loop 9 has been extended distally from the lumen 11 in the insertion rod 2, and has been manipulated by the surgeon to snare the ends 47 and 48. FIG. 4 illustrates that the snare and snare rod have been pulled proximally to draw the suture ends into the lumen 11, drawing the welding portions 45 and 46 into the space between the jaws. The snare rod has been rotated within the lumen to coil the fusing portions of the suture ends into a length of intertwined suture segments, referred to as the twist 49. In FIG. 5, the surgeon has closed the jaws upon the twist 49. The surgeon ensures that enough suture has been taken up in the twist so that the sutured incision is properly closed, tensioning the suture by a combination of pulling and twisting to draw the suture into the insertion rod. The suture may be tensioned as desired by the surgeon prior to melting by closing the jaws firmly on the suture while drawing the snare proximally, then closely the jaws tightly so that the suture is held in properly tensioned position while the weld is accomplished. The surgeon then applies heating power to the heating elements in the jaws by operating the switch 25 in the handle. The heat fuses the weld portions of each suture into mass that firmly holds the standing parts together, just as would a well tied knot. The closure of the jaws also forces the blade through the suture ends to cut away any excessive length of suture above the weld. (The blade may be omitted where the suture used with the device is easily separable during welding, so the formation of the weld also results in separation of the standing part from the loose ends. A light tension on the loose ends during welding is sufficient to separate some sutures.) When the jaws are opened, the melted twist is released from the jaws and remains in place within the body, just as would the knot. The severed suture ends 47 and 48 may be withdrawn from the device by pulling the snare rod completely out of the proximal end of the suture welding device. The sutures may be inserted into the snare using other endoscopic instruments inserted into the endoscopic workspace through other access ports, and the manipulations necessary to grab the suture and weld it at the proper place may be monitored with endoscopic cameras which are commonly used to visualized endoscopic procedures.

Figure 6:
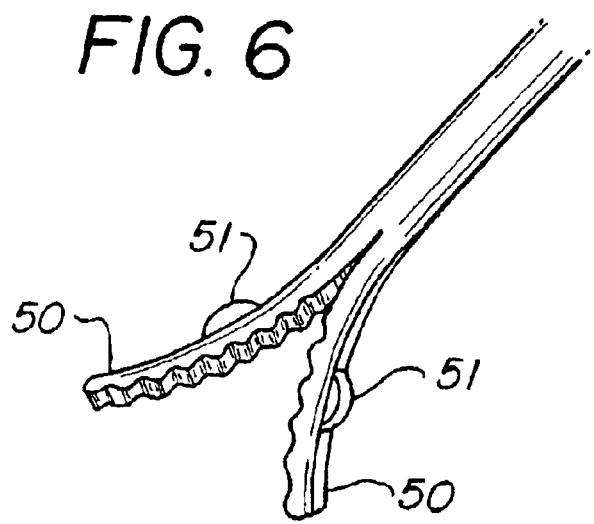
FIGS. 6 and 7 illustrate variations on the snare used with the suture welding device.
Figure 7:
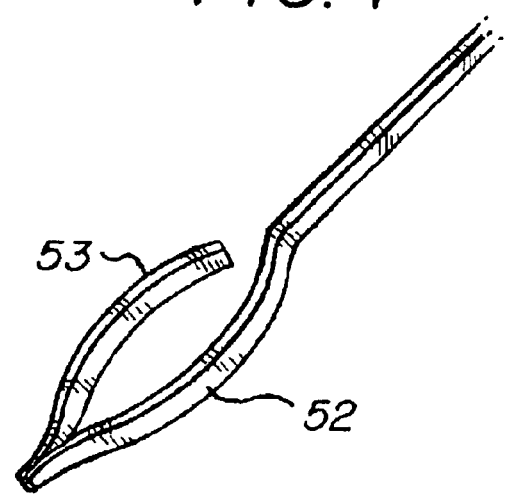

FIGS. 6 and 7 illustrate variations of the snare that may be used with the suture welding device. In FIG. 6, the snare is comprised of two diverging arms 50 extending from the snare rod and forming a Y together with the snare rod. The arms of the grasper may be closed upon withdrawal into the lumen of the insertion rod. The bosses 51 on the outer surface of each arm help urge the arms closed as they are impinged upon by the walls of the lumen. In FIG. 7, the snare is comprised of an arcuate branch 52 extending distally from the snare rod and a partial arcuate branch 53 extending proximally from the distal end of the first arcuate branch 52 back toward the snare rod. Many other embodiments of snares may be used.

Figure 8:
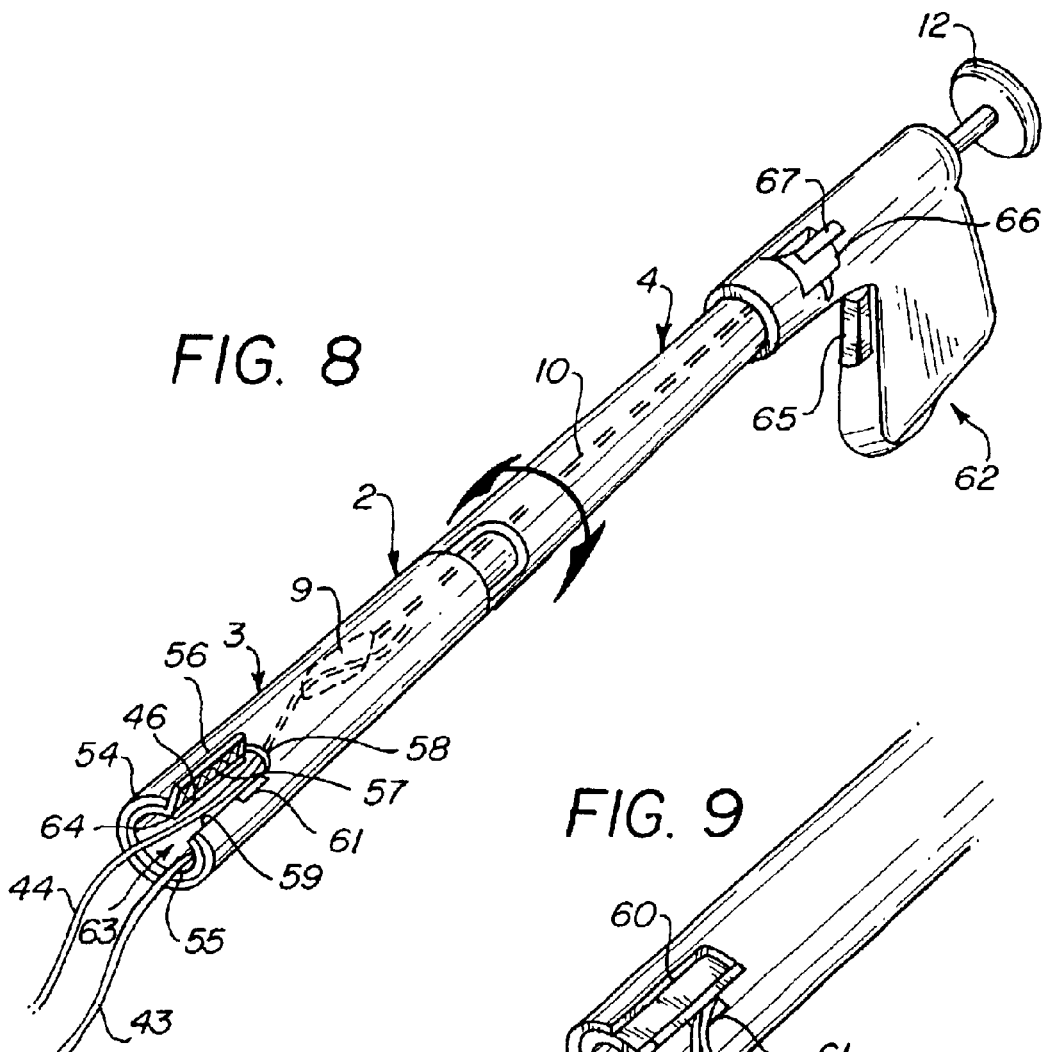
FIG. 8 illustrates a rotary embodiment of the suture welding device.

FIG. 8 illustrates a rotary embodiment of the suture welding device. The device comprises an insertion rod 2 with a distal end 3 and a proximal end 4. The outer tube 54 of the insertion rod houses an inner tube 55 which is rotatable within the outer tube. On the distal end of the inner tubes, heating anvil 56 and grasping surface 57 are formed from a radially extending boss. The inner and outer tubes have a small slot 58 which opens on the distal extremity of each tube. The slot defines longitudinally aligned slot wall 59 (visible in FIG. 8) and an opposing slot wall 60 (visible in FIG. 9) in the outer tube. A small notch 61 is located in the slot wall 59, opposite to the heating anvil, to receive and locate the suture in relation to the heating anvil. The heating anvil is mounting on one edge of the slot of the inner tube, and extends radially outwardly from the center axis of the tube and into the slot of the outer tube. The grasping surface of the outer tube is disposed on the slot wall of the outer tube slot which opposes the anvil, so that rotation of the inner tube rotates the anvil into mating relationship with the grasping surface of the outer tube. The proximal end of the insertion rod 2 is fitted with a handle assembly 62 which enables rotation of the inner tube 55 to bring the grasping boss 56 into contact or close proximity with the matching grasping surface 57 within the longitudinally aligned slot on the outer tube. A snare 10 is slidably and rotatably disposed within the insertion rod 2, within a lumen 63 in the inner tube 55. The snare 8 includes a snare structure 9 mounted on the distal end of the snare rod 10 and the handle 12 mounted on the distal end. The snare exits out the distal end of the insertion rod, and as illustrated exits through the open lumen of the inner tube. The snare is illustrated in the position within the inner tube, indicating that the surgeon has operated the snare to snare the suture ends, leaving the standing parts 43 and 44 outside the tube, and placing the welding portions 45 and 46 within the slot between the anvil and the grasping face. A cutting blade 64 is disposed on the inner edge of the heating anvil, and provides an easily accessible blade for cutting the suture ends from the weld. The handle assembly 62 includes a pistol grip with a trigger switch 65 which is operated by the surgeon to apply electrical energy to the anvil. An aperture 66 through the proximal end of the barrel 2 and handle assembly accommodates a boss 67 which protrudes from the inner tube 55. The boss is fixed to the inner tube, so that the surgeon may push the boss downward to rotate the inner tube, and thereby close the grasping boss 56 upon the matching grasping surface 57 to grasp and melt the suture as described above.

Figure 9:
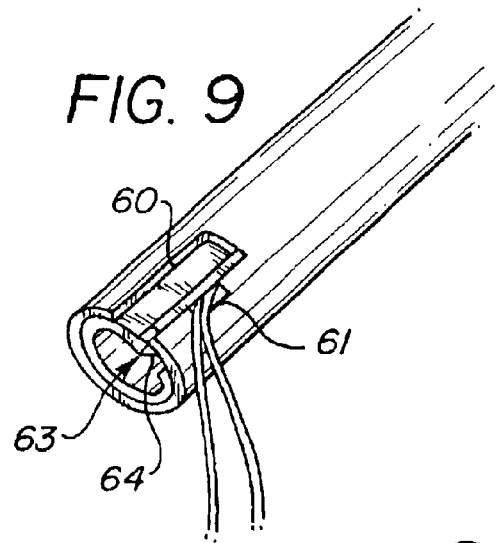
FIG. 9 illustrates a step in the operation of the suture welding device of FIG. 8.

FIG. 9 illustrates a step in the operation of the rotating suture welding device of FIG. 8. Again, the surgeon has tensioned the sutures as desired by pulling the appropriate amount of suture into the insertion rod and/or twisting the suture weld portions together. Tensioning can be accomplished by twisting the standing parts of the suture and/or drawing the suture proximally in to the rod until the desired degree of tension is obtained. The surgeon has drawn the suture end into the insertion rod, and has trapped the welding portions of the suture between the anvil 56 and the grasping surface 57 by rotating the inner tube relative to the outer tube. Closure of the anvil upon the grasping surface also results in closure of the blade 64 on the suture, severing the suture ends from the weld portions. (Again, the blade may be omitted where the suture used with the device is easily separable during welding, so the formation of the weld combined with light tension on the loose ends of the suture results in separation of the standing part from the loose ends.) The weld is made such that the standing portion is of appropriate tension. After the weld is complete, the suture ends may be removed be pulling the snare rod proximally from the device.

Figure 10:
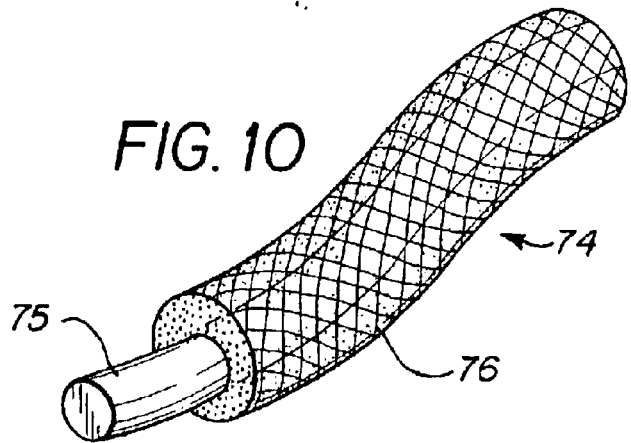
FIG. 10 is an illustration of the suture with a meltable component that may be used with the suture welding devices.

FIG. 10 illustrates the suture with a meltable component that may be used with the suture welding devices. The suture 74 is comprised of a meltable core 75 covered by a melt-resistant porous sheath 76. Upon application of heat sufficient to melt the core, the core material flows through the porous sheath and flows into core material flowing from adjoining suture segments. The temperature is maintained below the melting point of the sheath material, so that the sheath does not melt and remains in tact so that the suture does not break or separate upon melting of the core. Preferably, the core melts at temperatures above body temperature but below temperatures which would significantly damage surrounding body tissue, such as the range of 40° C. to 270° C. (these temperatures can be achieved briefly in the heating elements without causing harmful heating in the surrounding body tissue). The porous sheath preferably melts at temperatures above the temperature range in which the core melts, preferably being melt resistant to temperatures exceeding the melting temperature of the core material. The core may be made of the following materials: polyethylene (120° C.), polypropylene, nylon (200° C.), polyethylene terepthalate (255–270° C.), polyester, polytetrafluoroethylene (PTFE) and ePTFE (Teflon®), polyglycolic acid, polyvinylidene, polylecaprone, polydioxanone, polyglectin, polygalactin, polyvinylidene fluoride and many other thermoplastics. The porous sheath may be made of the materials such as silk, cotton, catgut, stainless steel, polyamide, PTFE, fluorinated ethylene propylene (FEP), and any one of the above-mentioned core materials that melts at a higher temperature than the selected core material. It should be appreciated that many combinations of core and porous sheath materials can be achieved.

Thus, while the preferred embodiments of the devices and methods have been described in reference to the environment in which they were developed, they are merely illustrative of the principles of the inventions. Other embodiments and configurations may be devised without departing from the spirit of the inventions and the scope of the appended claims.

We claim:

1. A device for securing a plurality of segments of suture together, said device comprising:
   an insertion rod having a distal end and a proximal end, said distal end adapted to be inserted into an endoscopic work space;
   a first means for grasping the suture, said first means being capable of snaring loose suture ends within an endoscopic work space, said first means for grasping being slidably disposed within the insertion rod and being operable from the proximal end of the insertion rod to grasp at least one segment of suture;
   a second means for grasping the suture operably attached to the insertion rod, said second means being disposed near the distal end of the insertion rod, said second means for grasping including means for heating the suture;

wherein the second means for grasping comprises:
a pair of grasping jaws disposed on the distal tip of the insertion rod, said jaws being operable from the proximal end of the insertion rod to open and close upon a segment of suture;
wherein the means for heating the suture comprises a heating element disposed on at least one of the grasping jaws;
wherein the a first means for grasping further comprises a snare rod slidably disposed within the insertion rod and operatively connected to the first means for grasping the suture, wherein the snare rod is operable from the proximal end of the insertion rod; and a plurality of diverging arms extending from the snare rod such that the two diverging arms form a Y-shape with the snare rod, wherein the diverging arms have an outer surface and an inner surface.

2. The device of claim 1 wherein the first means for grasping the suture further comprises at least one boss disposed on the outer surface of each arm.

3. A device for securing a plurality of segments of suture together, said device comprising:
a barrel having a distal end and a proximal end;
a first means for grasping the suture, said first means being capable of snaring loose suture ends, said first means for grasping being slidably disposed within the barrel and being operable from the proximal end of the barrel to grasp at least one segment of suture;
a second means for grasping the suture, said second means being disposed near the distal end of the barrel, said second means including means for heating the suture;
wherein the second means for grasping comprises:
a pair of grasping jaws disposed on the distal tip of the barrel, said jaws being operable from the proximal end of the barrel to open and close upon a segment of suture;
wherein the means for heating the suture comprises a heating element disposed on at least one of the grasping jaws;
wherein the first means for grasping the suture is operatively attached to a snare rod, wherein the snare rod is slidably disposed within the barrel and the snare rod is operable from the proximal end of the barrel;
a screw disposed on the snare rod such that rotating the screw also rotates the snare rod, said screw having a proximal end, a distal end, and threads; and
a slide yoke engaging the threads so that movement of the slide yoke causes rotation of the screw and the snare rod, said slide yoke being operable by a user.

4. The device of claim 3 further comprising:
a first stop plate disposed on the proximal end of the screw and disposed on the snare rod;
whereby when the yoke is drawn proximally against the stop plate, further proximal movement of the yoke pushes the first stop plate proximally into the barrel and thereby draws the snare rod into the barrel.

5. The device of claim 4 further comprising:
a second stop plate disposed in the proximal end of the barrel and proximal to the first stop plate, said second stop plate operatively connected to a means for closing the grasping jaws;
whereby when the first stop plate is drawn proximally against the second stop plate, further movement of the first stop plate proximally pushes the second stop plate and thereby causes the grasping jaws to close.

6. The device of claim 5 further comprising a biasing element operatively connected to the yoke, whereby the yoke is biased to move distally.

7. The device of claim 5 wherein the first means for grasping the suture comprises two arcuate branches, with each branch extending distally from the snare rod to curve first outwardly from the long axis of the snare rod and then inwardly towards the long axis of the snare rod such that each branch is joined together at their distal tips.

8. The device of claim 5 wherein the first means for grasping the suture comprises two diverging arms extending from the snare rod such that the two diverging arms form a Y-shape with the snare rod, wherein the diverging arms have an outer surface and an inner surface.

9. The device of claim 8 wherein the first means for grasping the suture further comprises at least one boss disposed on the outer surface of each arm.

10. The device of claim 5 wherein the first means for grasping the suture comprises:
a first arcuate branch extending distally from the snare rod; and
a second arcuate branch extending proximally from the distal end of the first arcuate branch, said second arcuate branch extending only partially towards the snare rod.

11. A method of securing a plurality of segments of suture together, said method comprising the steps of:
providing a device for securing a plurality of segments of suture together, said device comprising:
an insertion rod having a distal end and a proximal end, said distal end adapted to be inserted into an endoscopic work space;
a first means for grasping the suture, said first means being capable of snaring loose suture ends within an endoscopic work space, said first means for grasping being slidably disposed within the insertion rod and being operable from the proximal end of the insertion rod to grasp at least one segment of suture;
a second means for grasping the suture operably attached to the insertion rod, said second means being disposed near the distal end of the insertion rod, said second means including means for heating the suture;
snaring the loose ends of the suture with the first means for grasping the suture;
thereafter grasping the loose ends of the suture with the second means for grasping the suture; and
heating the loose ends of the suture until the loose ends melt together.

12. The method of claim 11 comprising the further step of:
before the step of grasping the loose ends of the suture with the second means for grasping the suture, drawing the loose ends of the suture into the insertion rod.

13. The method of claim 12 comprising the further step of:
before the step of grasping the loose ends of the suture with the second means for grasping the suture, twisting the loose ends of the suture into a twist.

* * * * *